US007507376B2

(12) United States Patent
Dufresne et al.

(10) Patent No.: US 7,507,376 B2
(45) Date of Patent: Mar. 24, 2009

(54) INTEGRATED SAMPLE PROCESSING DEVICES

(75) Inventors: Joel R. Dufresne, St. Paul, MN (US); David J. Franta, Woodbury, MN (US); Christopher R. Kokaisel, St. Paul, MN (US); Scott M. Lecy, Maplewood, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 1361 days.

(21) Appl. No.: 10/325,723

(22) Filed: Dec. 19, 2002

(65) Prior Publication Data

US 2004/0121471 A1 Jun. 24, 2004

(51) Int. Cl.
*B01L 3/00* (2006.01)
(52) U.S. Cl. ............................ 422/99; 422/102; 422/104
(58) Field of Classification Search ................ 422/99, 422/102, 104
See application file for complete search history.

(56) References Cited

U.S. PATENT DOCUMENTS

| 3,555,284 A | 1/1971 | Anderson |
| 3,795,451 A | 3/1974 | Mailen |
| 3,798,459 A | 3/1974 | Anderson et al. |
| 3,873,217 A | 3/1975 | Anderson et al. |
| 5,461,134 A | 10/1995 | Leir et al. |
| 6,004,512 A | 12/1999 | Titcomb et al. |
| 6,007,914 A | 12/1999 | Joseph et al. |
| 2002/0048533 A1 | 4/2002 | Harms et al. |
| 2002/0064885 A1 | 5/2002 | Bedingham et al. |

FOREIGN PATENT DOCUMENTS

| WO | WO 96/34028 A1 | 10/1996 |
| WO | WO 96/34029 | 10/1996 |
| WO | WO 96/35458 A2 | 11/1996 |
| WO | WO 00/68336 A1 | 11/2000 |
| WO | WO 02/01180 A2 | 1/2002 |
| WO | WO 02/01181 A2 | 1/2002 |

OTHER PUBLICATIONS

*Handbook of Pressure Sensitive Adhesive Technology*, Donatas Satas (Ed.), 2nd Edition, p. 172, 173, Van Nostrand Reinhold, New York, NY, 1989.
*Handbook of Pressure Sensitive Adhesive Technology*, Donatas Satas (Ed.), 3rd Edition, pp. 508-517, no date provided.
*Test Methods for Pressure Sensitive Adhesive Tapes*, Pressure Sensitive Tape Council, (1996).
Product Information Sheet for Microplates Height Dimensions (Draft), no date provided.
Product Information Sheet for Microplates Footprint Dimensions (Draft), no date provided.

*Primary Examiner*—Lyle A Alexander

(57) ABSTRACT

Sample processing devices may include compression structures that provide for the transfer of force from a platen to a platform such as a thermal block on which the sample processing device is located during processing. The sample processing devices may include a fill reservoir structure with various features such as arcuate edges, radially aligned exit channels, support structures, and selectively variable heights with a corresponding variable volume distribution.

10 Claims, 6 Drawing Sheets

INTEGRATED SAMPLE PROCESSING DEVICES

BACKGROUND

Modern scientific investigations frequently involve the use of large number of chemical reactions. For efficient implementation, these reactions are preferably run using systems that minimize setup times and cost while ensuring the quality of their results.

In many cases, a multiplicity of reactions are performed on systems in which a small set of reactants are combined with a much larger set of reactants. For example, a single biological sample may be subjected to a multiplicity of polymerase chain reactions, each of which address the expression level of a single gene.

Many different chemical, biochemical, and other reactions are also sensitive to small temperature variations. The reactions may be enhanced or inhibited based on the temperatures of the materials involved. In many such reactions, a temperature variation of even 1 or 2 degrees Celsius may have a significantly adverse impact on the reaction. Although it may be possible to process samples individually and obtain accurate sample-to-sample results, individual processing can be time-consuming and expensive.

One approach to reducing the time and cost of processing multiple samples is to use a device including multiple chambers in which different portions of one sample or different samples can be processed simultaneously. However, this approach presents several temperature control related issues. When using multiple chambers, the temperature uniformity from chamber to chamber may be difficult to control. Another problem involves the speed or rate at which temperature transitions occur when thermal processing, such as when thermal cycling. Still another problem is the overall length of time required to thermal cycle a sample(s).

The multiple chamber device may include a distribution system. However, the distribution system presents the potential for cross-contamination. Sample may inadvertently flow among the chambers during processing, thereby potentially adversely impacting the reaction(s) occurring in the chambers. This may be particularly significant when multiple samples are being processed. In addition, the distribution system may present problems when smaller than usual samples are available, because the distribution system is in fluid communication with all of the process chambers. As a result, it is typically not possible to prevent delivery of sample materials to all of the process chambers to adapt to the smaller volume samples.

Thermal processing, in and of itself, presents an issue in that the materials used in the devices may need to be robust enough to withstand repeated temperature cycles during, e.g., thermal cycling processes such as PCR. The robustness of the devices may be more important when the device uses a sealed or closed system. Also, it is often required that the process chambers remain in adequate alignment with instrument optics despite temperature changes and the attendant thermal expansion.

Various sample processing devices of the present invention are described in U.S. Provisional Patent Application Ser. No. 60/214,508 filed on 28 Jun. 2000 and titled THERMAL PROCESSING DEVICES AND METHODS; U.S. Provisional Patent Application Ser. No. 60/214,642 filed on 28 Jun. 2000 and titled SAMPLE PROCESSING DEVICES, SYSTEMS AND METHODS; U.S. Provisional Patent Application Ser. No. 60/237,072 filed on 2 Oct. 2000 and titled SAMPLE PROCESSING DEVICES, SYSTEMS AND METHODS; U.S. patent application Ser. No. 09/710,184, filed 10 Nov. 2000, titled CENTRIFUGAL FILLING OF SAMPLE PROCESSING DEVICES, U.S. patent application Ser. No. 09/895,001, filed 28 Jun. 2001, and titled SAMPLE PROCESSING DEVICES AND CARRIERS; U.S. patent application Ser. No. 09/895,010, filed 28 Jun. 2001, and titled SAMPLE PROCESSING DEVICES.

The documents identified above all disclose a variety of different constructions of sample processing devices that could be used to manufacture sample processing devices according to the principles of the present invention. For example, although many of the sample processing devices described herein are attached using adhesives (e.g., pressure sensitive adhesives), devices of the present invention could be manufactured using heat sealing or other bonding techniques.

Although the devices and their carriers identified in the above-listed patent documents may provide many advantages over the prior art, further improvements may still be possible. For example, the use of a carrier separate from the sample processing device may add cost to the sample processing devices as delivered to customers because of the need to manufacture different components separately from each other and then accurately assemble the components. In addition to adding cost, inaccurate assembly may cause performance problems due to misalignment of interrogation zones with the optics train of the analytical device. Further variability in the assembly process may induce unwanted part-to-part variability in the way the assembly fits to the thermal platen and hence thermal variations between process chambers.

SUMMARY OF THE INVENTION

The present invention provides integrated sample processing devices for thermal processing of multiple samples at the same time. The sample processing devices may include compression structures that provide for the transfer of force from a platen to a thermal block on which the sample processing device is located during processing. By distributing the compression structures over a compliant sample processing device, intimate contact between substantially all of the processing chambers in the sample processing device and the thermal block can be achieved in spite of variations in the thickness of the sample processing device due to, e.g., manufacturing tolerances.

Such compression structures may also be useful in ensuring that the reaction chambers of the sample processing device are located on a common plane during optical interrogations performed during, or after, thermal or other processing. For example, the sample processing devices may be thermally processed and then placed on an optical detection system for assessment of reaction products. This situation is encountered when performing "end-point reads" following thermal-cycling on Peltier blocks that do not provide for real-time monitoring of the processing, e.g., PCR.

In some embodiments, the compression structures may include permanently deformable compression structures that may help to equilibrate the force with which the processing chambers of the sample processing device are urged against a platen. The permanently deformable structures may include, e.g., frangible elements that permanently deform in a manner that provides an indication that a sample processing device has been used. The frangible element may, in some instances, include a chromic indicator that changes color when deformed to further enhance unaided visual determination of use of the sample processing device.

The sample processing devices may include a fill reservoir structure with various features such as arcuate edges, radially aligned exit channels, support structures, and selectively variable heights (and corresponding volume distribution) to enhance even distribution of fluid sample materials to the main channels and processing chambers of a sample processing device according to the present invention.

The sample processing devices of the present invention preferably have a form factor that is compatible with conventional microtiter plates such that conventional microtiter plate processing equipment and systems may be used to process sample processing devices of the present invention. For example, it may be preferred that that the sample processing devices have a height of five millimeters or more. Furthermore, it may be preferred that that the sample processing devices of the present invention have a maximum height as defined by the Society for Biomolecular Screening Standard "SBS-2 for Microplates—Height Dimensions" (9 May 2002).

A further advantage of the present invention may come from more precise control of fill port locations. The use of multiple fill ports on a sample processing device is particularly advantageous if the fill ports are compatible with standard laboratory robotic equipment for liquid dispensing. For example, eight or more micropipettes are frequently arranged in a linear array with uniform spacing to efficiently fill standard microplates. Use of such micropipette arrays to fill particular embodiments of the present invention could provide a significant benefit to users requiring highly automated laboratory operations using existing equipment.

Use of the present invention with such automated operations is further facilitated if the particular embodiment complies with the standardized form-factor for microplates. In such cases, the handling of the microplate subsequent to loading can be performed by commonly available robotic equipment.

Finally, because many of the reactants used with the present invention are often expensive and available only in small quantities, it is important to utilize sample processing devices which minimize the amounts of samples necessary to achieve satisfactory results. In particular, this requires loading mechanisms which efficiently distribute the sample to each of the reaction chambers and that reduce the risk of spillage during loading and handling of the devices.

In some embodiments, the sample processing devices may include multiple parallel fill reservoirs that are in fluid communication with each other through a fluid path.

Methods of using such sample processing devices may include occluding those fluid paths to isolate the fill reservoirs after manufacturing the sample processing devices. The fill reservoirs may preferably have fill ports proximate the outermost edges of the sample processing device such that a sample processing device including fill reservoirs filled with sample materials may be stood on edge without leaking the sample materials from the fill reservoirs.

The sample processing devices of the present invention may also include deformable seals to occlude channels used to distribute sample materials from the fill reservoirs to the process chambers. Deformable seals may also provide for isolation of the process chambers located along the channels, such that chemical cross-contamination (e.g., migration of reagents or reaction products between process chambers after introduction of sample material) may be reduced or eliminated, particularly during sample processing, e.g. thermal cycling. Deformable seals may also provide the opportunity to tailor the devices for specific test protocols by closing the channels leading to selected process chambers before distributing sample materials. Alternatively, some deformable seals may be closed to adjust for smaller sample material volumes reducing the number of process chambers to which the sample materials are distributed.

It is preferred that sample processing devices of the invention exhibit robustness in response to the rapid thermal changes that can be induced due to the relatively high thermal conductivity and relatively low thermal mass of the devices. This robustness may be particularly valuable when the devices are used in thermal cycling methods such as, e.g., PCR. In all thermal processing methods, the preferred devices maintain process chamber integrity despite any pressure changes that may be associated with the temperature variations and despite the differences between thermal expansion rates of the various materials used in the devices.

As used in connection with the present invention, the following terms shall have the meanings set forth below.

"Deformable seal" (and variations thereof) means a seal that is permanently deformable under mechanical pressure (with or without a tool) to occlude a conduit along which the deformable seal is located.

"Thermal processing" (and variations thereof) means controlling (e.g., maintaining, raising, or lowering) the temperature of sample materials to obtain desired reactions. As one form of thermal processing, "thermal cycling" (and variations thereof) means sequentially changing the temperature of sample materials between two or more temperature setpoints to obtain desired reactions. Thermal cycling may involve, e.g., cycling between lower and upper temperatures, cycling between lower, upper, and at least one intermediate temperature, etc.

In one aspect, the present invention provides a method of processing sample materials by providing a sample processing device including a body having a first major side and a second major side; a base sheet attached to the first major side of the body, and a plurality of compression structures protruding from the second major side of the body, wherein the body and the base sheet define one or more fill reservoirs, a plurality of process chambers, and a plurality of channels, wherein each channel of the plurality of channels is in fluid communication with at least one fill reservoir of the one or more fill reservoirs, and wherein each process chamber of the plurality of process chambers is in fluid communication with at least one channel of the plurality of channels. The method includes distributing sample material to at least some process chambers of the plurality of process chambers; locating the base sheet of the sample processing device in contact with a thermal block; contacting the second major side of the body with a platen to urge the base sheet of the sample processing device into intimate contact with the thermal block; and permanently deforming at least some of the plurality of compression structures protruding from the second major side of the body while contacting the second major side of the body with the platen. The temperature of the thermal block is controlled while the sample processing device is in contact with the thermal block.

In another aspect, the present invention provides a method of processing sample materials by providing a sample processing device including a body having a first major side and a second major side; a base sheet attached to the first major side of the body, and a plurality of compression structures protruding from the second major side of the body, wherein the body and the base sheet define one or more fill reservoirs, a plurality of process chambers, and a plurality of channels, wherein each channel of the plurality of channels is in fluid communication with at least one fill reservoir of the one or more fill reservoirs, and wherein each process chamber of the plurality of process chambers is in fluid communication with at least one channel of the plurality of channels, and wherein the body includes a frame proximate a perimeter of the body, the frame defining a frame volume, wherein the one or more fill reservoirs are located within the frame volume. The method further includes distributing sample material to at least some process chambers of the plurality of process chambers; locating the base sheet of the sample processing device in contact with a thermal block; contacting the second major side of the body with a platen to urge the base sheet of the sample processing device into intimate contact with the thermal block; permanently deforming all of the compression structures protruding from the second major side of the body while contacting the second major side of the body with the platen; and controlling the temperature of the thermal block while the sample processing device is in contact with the thermal block. Each compression structure of the plurality of compression structures includes a post extending from the first major surface to the second major surface of the body, wherein contacting the second major side of the body with a platen to urge the base sheet of the sample processing device into intimate contact with the thermal block transfers force from the platen to the thermal block. The method includes permanently deforming a frangible indicator element on at least some of the plurality of compression structures.

In another aspect, the present invention includes a method of interrogating a sample processing device by providing a sample processing device including a body having a first major side and a second major side; a base sheet attached to the first major side of the body, and a plurality of compression structures protruding from the second major side of the body, wherein the body and the base sheet define a plurality of process chambers with sample material located in at least some process chambers of the plurality of process chambers. The method includes locating the base sheet of the sample processing device in contact with an interrogation platform; contacting the second major side of the body with a platen to urge the base sheet of the sample processing device into intimate contact with the interrogation platform; permanently deforming at least some of the plurality of compression structures protruding from the second major side of the body while contacting the second major side of the body with the platen; and interrogating at least some of the process chambers while the sample processing device is in contact with the interrogation platform.

In another aspect, the present invention provides a method of manufacturing a sample processing device by providing a body having a first major side and a second major side, a plurality of isolated fill reservoir structures located between the first major side of the body and the second major side of the body; a plurality of process chamber structures formed into the first major side of the body; and a plurality of channel structures formed into the first major side of the body. The method further includes opening a fluid path between at least one pair of adjacent isolated fill reservoir structures, wherein the number of isolated fill reservoir structures is reduced; attaching a base sheet to the first major side of the body, wherein the body and the base sheet define one or more fill reservoirs, a plurality of process chambers structures, and a plurality of channels, wherein each channel of the plurality of channels is in fluid communication with at least one fill reservoir of the one or more fill reservoirs, and wherein each process chamber of the plurality of process chambers is in fluid communication with at least one channel of the plurality of channels.

In another aspect, the present invention provides a sample processing device including a body having a first major side and a second major side; one or more fill reservoir structures located between the first major side of the body and the second major side of the body; a plurality of process chamber structures formed into the first major side of the body; a plurality of channel structures formed into the first major side of the body; a plurality of compression structures protruding from the second major side of the body, wherein the plurality of compression structures include frangible indicator elements proximate the second major side of the body; and a base sheet attached to the first major side of the body, wherein the base sheet and the one or more fill reservoir structures define one or more fill reservoirs in the device, wherein the base sheet and the plurality of process chamber structures define a plurality of process chambers in the device, and wherein the base sheet and the plurality of channel structures define a plurality of channels in the device, wherein each channel of the plurality of channels is in fluid communication with at least one fill reservoir of the one or more fill reservoirs, and wherein each process chamber of the plurality of process chambers is in fluid communication with at least one channel of the plurality of channels.

In another aspect, the present invention provides a sample processing device including a fill reservoir; a plurality of process chambers; and a plurality of channels. Each channel of the plurality of channels is in fluid communication with the fill reservoir and each process chamber of the plurality of process chambers is in fluid communication with at least one channel of the plurality of channels. The fill reservoir has an arcuate edge, wherein each channel of the plurality of channels exits the fill reservoir from the arcuate edge of the fill reservoir and extends in a direction normal to a tangent of the arcuate edge for a first portion of the length of the channel, and wherein the plurality of channels are aligned with a longitudinal axis for a second portion of the length of the channel.

In another aspect, the present invention provides a sample processing device having a fill reservoir; a plurality of process chambers; and a plurality of channels. Each channel of the plurality of channels is in fluid communication with the fill reservoir and each process chamber of the plurality of process chambers is in fluid communication with at least one channel of the plurality of channels. The fill reservoir has an axis of symmetry and includes a fill port proximate the axis of symmetry, with two or more vent ports arranged symmetrically about the axis of symmetry.

In another aspect, the present invention provides a sample processing device including a fill reservoir; a plurality of process chambers; and a plurality of channels. Each channel of the plurality of channels is in fluid communication with the fill reservoir and each process chamber of the plurality of process chambers is in fluid communication with at least one channel of the plurality of channels. The fill reservoir includes a selectively varied height between two sides of the fill reservoir such that a desired distribution of the volume of the fill reservoir is provided.

In another aspect, the present invention provides a sample processing device including a fill reservoir; a plurality of process chambers; and a plurality of channels. Each channel of the plurality of channels is in fluid communication with the fill reservoir and each process chamber of the plurality of process chambers is in fluid communication with at least one channel of the plurality of channels. The device further includes one or more support structures located within the fill reservoir, wherein the support structures maintain spacing between two opposing sides of the fill reservoir. The fill reservoir also includes an arcuate edge, wherein each channel of the plurality of channels exits the fill reservoir from the arcuate edge of the fill reservoir and extends in a direction normal to a tangent of the arcuate edge for a first portion of the length of the channel, and wherein the plurality of channels are aligned with a longitudinal axis for a second portion of the length of the channel. The fill reservoir also includes an axis of symmetry with a fill port proximate the axis of symmetry and two or more vent ports arranged symmetrically about the axis of symmetry. The two or more vent ports are located on a side of the vent port that is opposite from the side on which the channels are located. The vent ports are in fluid communication with the fill reservoir through vent channels, with the vent channels connected to the fill reservoir at points symmetrical with the axis of symmetry. The fill reservoir also includes outer edges distal from the axis of symmetry and a selectively varied height between two sides of the fill reservoir, and wherein the height of the fill reservoir proximate the outer edges is greater than the height of the fill reservoir proximate the axis of symmetry such that a desired distribution of the volume of the fill reservoir is provided.

In other aspect, the present invention provides methods of processing sample materials using the sample processing devices described herein that includes loading the fill reservoir with sample material and rotating the sample processing device about an axis of rotation located proximate a center defined by the arcuate edge of the fill reservoir and the first portions of the channels (if present), whereby the sample material is distributed to the plurality of process chambers.

These and other features and advantages of the present invention are described below in connection with various illustrative embodiments of the devices and methods of the present invention.

DETAILED DESCRIPTION OF ILLUSTRATIVE EMBODIMENTS OF THE INVENTION

The present invention provides a sample processing device that can be used in the processing of liquid sample materials (or sample materials entrained in a liquid) in multiple process chambers to obtain desired reactions, e.g., PCR amplification, ligase chain reaction (LCR), self-sustaining sequence replication, enzyme kinetic studies, homogeneous ligand binding assays, and other chemical, biochemical, or other reactions that may, e.g., require precise and/or rapid thermal variations. The sample processing devices include one or more fill reservoirs, a plurality of process chambers, and at least one channel placing the process chambers in fluid communication with a fill reservoir.

Figure 1:
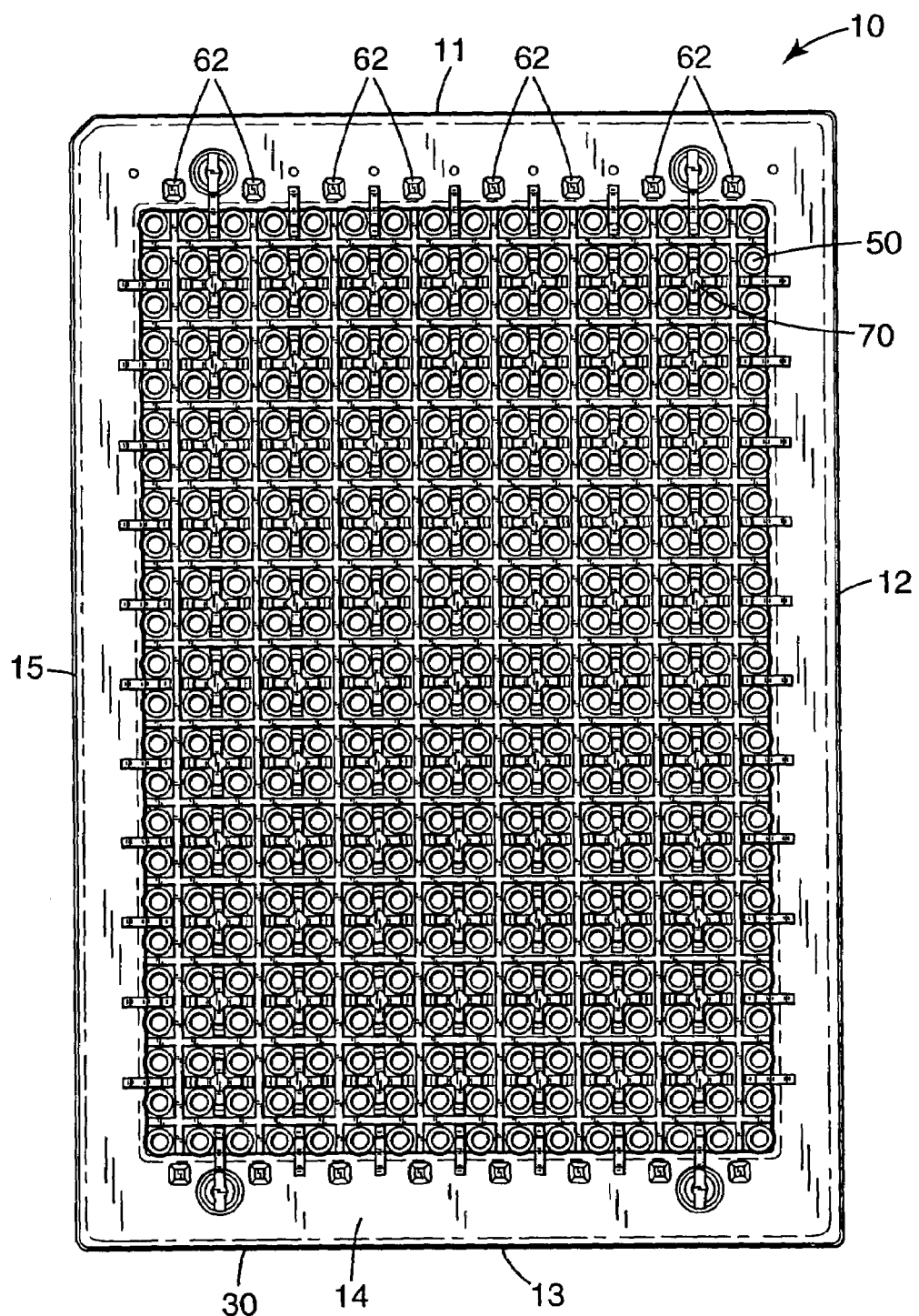
FIG. 1 is a top plan view of the top side of one sample processing device of the invention.
Figure 2:
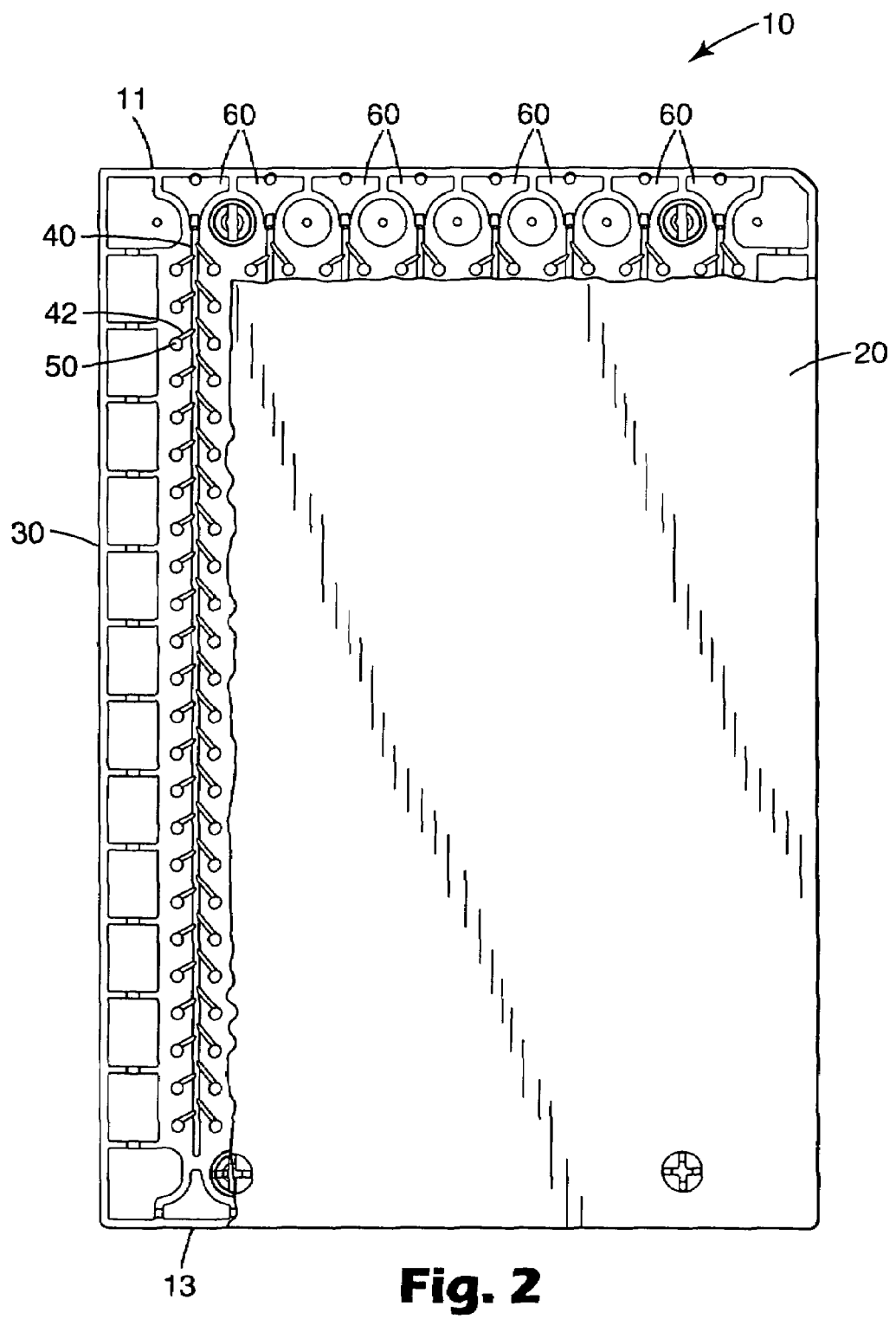
FIG. 2 is a bottom plan view of the bottom side of the body of the sample processing device depicted in FIG. 1 (with a portion of the base sheet removed to expose a portion of the bottom side of the body).

One illustrative sample processing device manufactured according to the principles of the present invention is illustrated in FIGS. 1 and 2, where FIG. 1 is a plan view of one major side of the sample processing device 10 and FIG. 2 is a plan view of the opposing major side of the sample processing device 10.

The side depicted in FIG. 1 will be described as the top side and the side depicted in FIG. 2 will be described as the bottom side, but it should be understood that relative positional terms such as "top" and "bottom" are used herein only to indicate that the two sides are on opposite sides of the sample processing device 10. Those terms should not be construed as limiting the present invention. For example, the top side as seen in FIG. 1 may actually be located beneath the bottom side as seen in FIG. 2 when the device is in actual use to process sample material.

The sample processing device 10 as seen in FIG. 1 includes a first edge 11 and an opposing second edge 13. A frame 14 extends around the perimeter of the sample processing device 10. Although the frame 14 is depicted as extending around the entire perimeter of the sample processing device 10, it should be understood that the frame 14 may be provided in the form of discontinuous segments that, taken as a whole, assist in defining the perimeter of the sample processing device 10.

The frame 14 also includes a sides 12 and 15 on which a bar code or other indicia can be located to assist in identifying the sample processing device 10 and/or its contents during use. The opposing sides 12 and 15 can, together, provide opposed parallel planar surfaces that facilitate gripping and manipulation of the sample processing device 10 by, e.g., a fingers of a user, a robotic manipulator, etc.

Also seen in FIG. 1 are fill ports 62 used to load sample materials into the fill reservoirs (described further below) that, in the depicted embodiment, are located within the frame 14.

The process chambers 50 are distributed over the top side of the sample processing device 10 within the perimeter of the sample processing device 10, which, in the case of the depicted embodiment, is within the boundaries of the frame 14. It may be preferred that the process chambers 50 be arranged in a rectilinear grid array as shown to facilitate interrogation and/or monitoring of the process chambers 50.

Also depicted in FIG. 1 are the compression structures 70 located within the array of process chambers 50. As discussed herein, the compression structures 70 may provide one or more of a number of different functions. For example, the compression structures 70 may be used to transfer force from the top side of the sample processing device 10 to the bottom side of the sample processing device 10, they may be used to equilibrate the applied force over the array of process chambers 50, they may be used to provide an indication that the sample processing device 10 has been used, etc.

It may be preferred that the compression structures 70 be distributed throughout the array of process chambers 50 such that substantially all of the process chambers 50 are located near at least one compression structure 70. For the purposes of the present invention, "near" will be defined as located with no more than one process chamber 50 between the process chamber 50 of interest and the closest compression structure 70. In the case of a sample processing device 10 in which the process chambers 50 are arranged in a rectilinear array, the compression structures 70 and process chambers 50 may be arranged such that all of the process chambers 50 are located adjacent at least one compression structure (with the possible exception of those four process chambers 50 located at the extreme corners of the array which are located "near" a compression structure 70). It may be preferred that the process chambers 50 are each equidistant from at least one compression structure 70.

By distributing the compression structures 70 over the array of process chambers 50, uniformity in the processing of sample materials within the process chambers may be enhanced.

FIG. 2 depicts the bottom side of the body of the sample processing device 10. The sample processing device 10 will typically include a base sheet 20 attached to the bottom side of the body 30, with the base sheet 20 being located over substantially all of the bottom side of the body 30. Because the base sheet 30 may typically be opaque, a substantial portion of it is removed in FIG. 2 so that the features formed in the bottom side of the body 30 can be seen.

Fill reservoir structures 60 can be seen in FIG. 2 located proximate the edge 11 of the sample processing device 10. Fill ports 62 used to load sample material in the fill reservoir structures 60 can be seen within the fill reservoir structures 60. The fill reservoir structures 60 depicted in FIG. 2 are only one embodiment of a fill reservoir structure that may be used in connection with a sample processing device of the present invention.

As described in connection with FIG. 2, the various features are defined as "structures" with the understanding that, until the base sheet 30 is attached to the bottom side of the body 30, the various structures do not completely form their respective features. For example, until the base sheet 30 is attached, the fill reservoir structures 60 as seen in FIG. 2 do not form a completed fill reservoir. It may be preferred that all of the structures forming the fill reservoirs 60, process chambers 50, main channels 40 and feeder channels 42 be formed into the bottom side of the body 30 while the base sheet 20 is provided in the form of a generally flat sheet.

Each of the fill reservoir structures 60 is in fluid communication with a main channel structure 40 that extends away from the fill reservoir structure 60 in the general direction of the opposing edge 13. The main channel structure 40 leads to feeder channel structures 42 that, in turn, lead to a process chamber structure 50. Each of the main channel structures 40 leads to multiple process chamber structures 50.

Together, each collection of a fill reservoir structure 60, main channel structure 40, feeder channel structures 42, and process chamber structures 50 can be described as forming a process array on the sample processing device 10. It may be preferred that, as depicted in FIG. 2, each of the process arrays include only one fill reservoir structure 60 and only one main channel structure 40. It may be preferred that the fill reservoir volume, i.e., the volume defined by the fill reservoir (if so provided), be equal to or greater than the combined volume of the main channel 40, process chambers 50, and feeder conduits 42 (if any). If desired, each of the process arrays may also include an optional drain chamber (not shown) located at the end of the main channel 40 opposite the fill reservoir 60.

In the depicted embodiment, the fill reservoirs 60 are located within the volume defined by the frame 14. Locating the fill reservoirs within that volume may provide a number of advantages. For example, the fill reservoirs 60 may be more robust, i.e., be less susceptible to damage during handling, the sample processing device 10 may be more compact, etc.

Another advantage of locating the fill reservoirs 60 within the volume of the frame 14 is that fill ports 62 (see FIG. 1) are also located within the frame 14. By locating the fill ports 62 within the frame 14, more precise control over the location and size of the fill ports 62 may be obtained because of the rigidity provided by a structure such as a frame 14. That increased control may be particularly advantageous if the sample processing device 10 is to be used with automated filling equipment that requires precise control over the location of the fill ports 62.

The sample processing device 10 includes at least one, and preferably a plurality of process arrays. Each of the depicted process arrays extends from proximate a first edge 11 towards the second edge 13 of the sample processing device 10. The process arrays are depicted as being substantially parallel in their arrangement on the sample processing device 10. Although this arrangement may be preferred, it will be understood that any arrangement of process arrays may alternatively be provided.

Alignment of the process arrays may be important if the main channels 40 of the process arrays are to be closed simultaneously as discussed in more detail below. Alignment of the process arrays may also be important if sample materials are to be distributed throughout the sample processing device by rotation about an axis of rotation proximate the first edge 11 of the sample processing device 10. When so rotated, any sample material located proximate the first edge 11 is driven toward the second edge 13 by centrifugal forces developed during the rotation.

The fill reservoir 60 may be designed to mate with an external apparatus (e.g., a pipette, hollow syringe, or other fluid delivery apparatus) to receive the sample material. The fill reservoir 60 itself may define a volume (as depicted). Alternatively, the fill reservoir may define no specific volume, but, instead, be a location at which sample material is to be introduced. For example, the fill reservoir 60 may be merely a fluid path or port through which a pipette or needle is to be inserted.

Although the depicted fill reservoirs 60 include fill ports 62, it should be understood that the fill ports 62 are optional. It may be preferred to provide loading structures that do not include pre-formed fill ports. In such a device, sample material may be introduced into the fill reservoir by piercing the fill reservoir with, e.g., a syringe. It may be desirable to use the syringe or another device to pierce the fill reservoir in a one location before piercing the fill reservoir in a second location to fill the reservoir. The first opening can then serve as a vent port to allow air (or any other gas) within the fill reservoir to escape during loading of the sample material. It may also be preferred to have multiple fill ports in each fill reservoir, with at least one fill port functioning as a vent during the loading process.

After loading, it may be preferred that the fill ports 62 be sealed by to prevent leakage of the sample material. One example of a suitable seal mechanism may be, e.g., a pressure sensitive adhesive tape.

Each of the process arrays in the sample processing devices 10 of the present invention may preferably be unvented. As used in connection with the present invention, an "unvented" process array is a process array in which the only ports leading into the volume of the process array are located in a fill reservoir of the process array. In other words, to reach the process chambers within an unvented process array, sample materials must be delivered through the fill reservoir. Similarly, any air or other fluid located within the process array before loading with sample material must also escape from the process array through the fill reservoir. In contrast, a vented process array would include at least one opening outside of the fill reservoir. That opening would allow for the escape of any air or other fluid located within the process array during distribution of the sample material within the process array.

Methods of distributing sample materials by rotating a sample processing device about an axis of rotation located proximate the loading structures are described in U.S. patent application Ser. No. 09/710,184, filed Nov. 10, 2000, titled CENTRIFUGAL FILLING OF SAMPLE PROCESSING DEVICES; U.S. patent application Ser. No. 09/895,001, filed 28 Jun. 2001, and titled SAMPLE PROCESSING DEVICES AND CARRIERS (corresponding to International Publication No. WO 02/01181 A2 (Bedingham et al.); and U.S. patent application Ser. No. 09/895,010, filed 28 Jun. 2001, and titled SAMPLE PROCESSING DEVICES (corresponding to International Publication No. WO 02/01180 A2 (Bedingham et al.).

It may be preferred that, regardless of the exact method used to deliver sample materials to the process chambers through the main channels of sample processing devices of the present invention, the result may be that substantially all of the process chambers, main channel, and feeder channels (if any) are filled with the sample material.

The process arrays depicted in FIG. 2 are arranged with the process chambers 50 located in two groups on both sides of each of the main channels 40. Many different variations in the arrangement of the process chambers 50, main channels 40 and feeder channels 42 are described in U.S. patent application Ser. No. 09/710,184, filed Nov. 10, 2000, titled CENTRIFUGAL FILLING OF SAMPLE PROCESSING DEVICES; U.S. patent application Ser. No. 09/895,001, filed 28 Jun. 2001, and titled SAMPLE PROCESSING DEVICES AND CARRIERS (corresponding to International Publication No. WO 02/01181 A2 (Bedingham et al.); and U.S. patent application Ser. No. 09/895,010, filed 28 Jun. 2001, and titled SAMPLE PROCESSING DEVICES (corresponding to International Publication No. WO 02/01180 A2 (Bedingham et al.).

It may be preferred to maintain the size of the main channels 40 and the feeder channels 42 as small as possible while still allowing for adequate sample material delivery and sufficient distance between the process chambers 50 to limit diffusion. Reducing the size of the channels 40 and 42 limits "channel volume" within the process arrays, where channel volume is the combined volume of the main channel 40 and the feeder channels 42 (where present), i.e., channel volume does not include the volume of the process chambers 50. It may be desirable to limit the ratio of channel volume to the total process chamber volume (i.e., the combined volume of all of the process chambers in the subject process array) to about 2:1 or less, alternatively about 1:1 or less, 1:2 or less, or even 1:3 or less.

One manner in which channel volume can be limited is to reduce the cross-sectional area of the main channel 40 and/or the feeder channels 42 (if present in the device). It may be possible to provide feeder channels 42 with a smaller cross-sectional area than the main channel 40 because of the reduced length of the feeder channels 42 as compared to the main channel 40 (making flow restriction less of a concern in the feeder channels).

Figure 3:
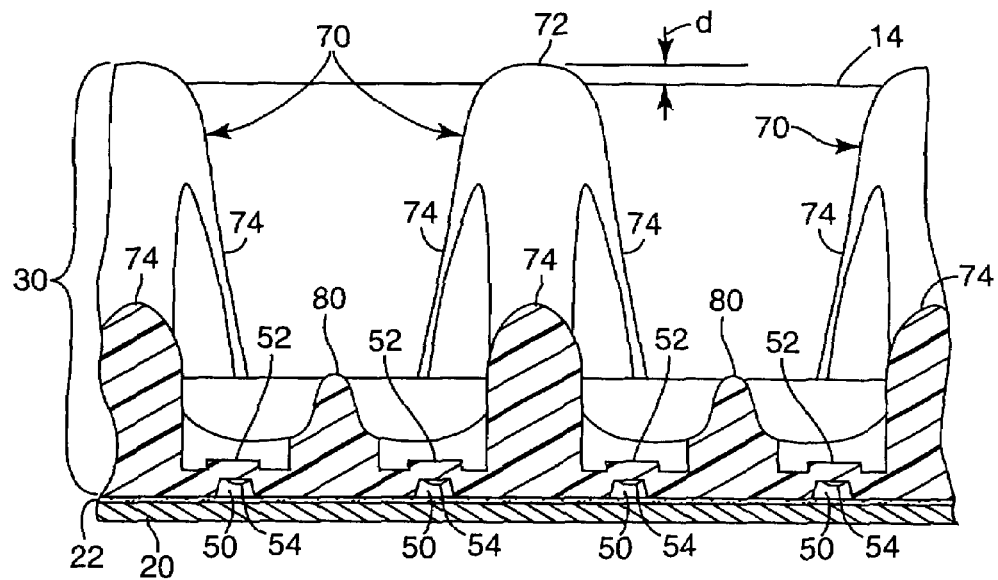
FIG. 3 is an enlarged cross-sectional view of a portion of the sample processing device of FIG. 1 depicting process chambers, compression structures and a portion of the frame.

Turning now to FIG. 3, which is an enlarged cross-sectional view of a portion of the sample processing device 10 of FIG. 1 depicting the body 30 including process chambers 50, compression structures 70 and a portion of the frame 14. A base sheet 20 is attached to the bottom side of the body 30.

The compression structures 70 each include a peak 72 that is distal from the bottom side of the body 30. In the depicted embodiment, the compression structures 72 include one or more ribs 74, with the majority of compression structures 70 including four ribs 74 that distribute a force applied on the peak of the compression structure over a wider area on the bottom side of the body 30. In FIG. 3, the rib 74 extending out of the paper is shown in partial cross-section.

In a sample processing device 10 that includes a frame 14, it may be preferred that the compression structures extend above or protrude from a plane that is defined by the uppermost surface of the frame 14. In FIG. 3, the peaks 72 of the compression structures 70 are located a distance (d) above the frame 14 (or the plane defined by the frame 14). By extending above the frame 14 or any other structure on the sample processing device 10, the compression structures 70 are assured of contacting, e.g., a platen or other device used to force the base sheet 20 against, e.g., a thermal block.

Pairs of adjacent process chambers 50 that are not separated from each other by a rib 74 of one of the compression structures 70 are separated from each other on the top side of the body by a wall 80. In the depicted embodiment, a series of walls 80 are provided in a rectilinear grid array (see, e.g., FIG. 1) that can perform a variety of functions.

Some of the walls 80 may be aligned opposite the main channels 40 on the bottom side of the body 30 to provide additional rigidity to the body during staking or closure of the channels as described in more detail below. The grid of walls 80 may provide additional rigidity to the body as a whole in addition to providing support above the main channels 40.

The walls 80 may optionally provide some measure of isolation to reduce optical cross-talk between process chambers 50 by providing a barrier to the transmission of electromagnetic energy (e.g., light) between the process chambers 50 during processing and/or interrogation of the process chambers 50. For example, the walls 80 may be opaque to electromagnetic radiation of selected wavelengths. Alternatively, the walls may merely inhibit the transmission of electromagnetic radiation of selected wavelengths by diffusion and/or absorption. For example, the walls 80 may include textured surfaces to enhance scattering, the walls 80 may include materials incorporated into the body of the wall 80 and/or provided in a coating thereon that enhance absorption and/or diffusion of selected wavelengths of electromagnetic energy.

Each of the process chambers 50 may include a reagent 54. It may be preferred that at least some, and preferably all, of the process chambers 50 in the devices 10 of the present invention contain at least one reagent before any sample material is distributed. The reagent 54 may be fixed within the process chamber 50 as depicted in FIG. 3. The reagent 54 is optional, i.e., sample processing devices 10 of the present invention may or may not include any reagents 54 in the process chambers 50. In another variation, some of the process chambers 50 may include a reagent 54, while others do not. In yet another variation, different process chambers 50 may contain different reagents.

The process chamber 50 also defines a volume. In sample processing devices of the present invention, it may be preferred that the volume of the process chambers be about 5 microliters or less, alternatively about 2 microliters or less, and, in yet another alternative, about 1 microliter or less. Providing sample processing devices with micro-volume process chambers may be advantageous to reduce the amount of sample material required to load the devices, reduce thermal cycling time by reducing the thermal mass of the sample materials, etc.

Figure 4:
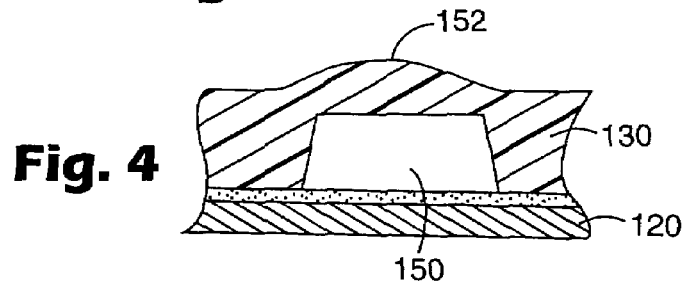
FIG. 4 is an enlarged cross-sectional view of an alternative process chamber incorporating a lens.

Each of the process chambers 50 includes a window 52 through which materials in the process chamber 50 may be interrogated and/or monitored. Referring to FIG. 4, an alternative process chamber 150 formed by a body 130 and a base sheet 120 is depicted and includes a window 152 that is shaped to focus electromagnetic energy entering the process chamber 150 and/or to collimate or focus electromagnetic energy exiting the process chamber 150 through window 152. As a result, the window 152 operates as a lens. In some instances, separate lenses may be insert-molded into the sample processing device as a part of each process chamber.

The sample processing devices may also include one or more features to facilitate optical interrogation of the process chambers by an associated instrument platform. Those features may include, e.g., pins or recesses that align with corresponding structures on the instrument, optical elements integrated with the process chambers which modify the optical path between the instrument and chemistries within the chambers, texturing or coloration of areas surrounding the process chambers which reduce optical "cross-talk" between adjacent chambers, etc.

The body 30 of the sample processing device 10 may be manufactured of any suitable material or materials. Examples of suitable materials include moldable materials, e.g., polymeric materials (such as polypropylene, polyester, polycarbonate, polyethylene, etc.), ceramic materials, metals, etc. It may, for example, be preferred that the body 30 be manufactured by injection molding of a polymeric material.

The base sheet 20 can be, e.g., a sheet of metal foil, polymeric material, multi-layer composite, etc. that is attached to the bottom side of the body 30 to complete formation of the process array features. It may be preferred that the materials selected for both the body 30 and the base sheet 20 exhibit good water barrier properties. It may be preferred that the materials selected for the base sheet 20 be deformable.

It may be preferred that at least one of the body 30 and the base sheet 20 be constructed of a material or materials that substantially transmit electromagnetic energy of selected wavelengths. For example, it may be preferred that one or both of the body 30 and the base sheet 20 be constructed of materials that allow for visual or machine monitoring of fluorescence and/or color changes within the process chambers 50.

It may also be preferred that at least one of the body 30 and the base sheet 20 include a metallic layer, e.g., a metallic foil. If a metallic foil is used to form the base sheet 20, a passivation layer may be provided on at least the surfaces of the base sheet 20 that face the interiors of the fill reservoirs 60, main channels 40, feeder channels 42, and/or process chambers 50 to prevent contamination of the sample materials by the metal.

As an alternative to a separate passivation layer, any adhesive layer 22 used to attached the base sheet 20 to the body 30 may also serve as a passivation layer to prevent contact between the sample materials and any metals in the base sheet 20. The adhesive may also be beneficial in that it may be conformable. If so, the adhesive may provide enhanced occlusion by filling and/or sealing irregularities or surface roughness present on the body 30 or the base sheet 20.

In the illustrative embodiment of the sample processing device depicted in FIG. 3, the body 30 may be injection molded polypropylene and the base sheet 20 may be a metallic foil, e.g., an aluminum or other metal foil. The metallic foil is preferably deformable as discussed in more detail herein.

In the depicted embodiment, the base sheet 20 is attached to the body 30 using a layer of adhesive 22. In place of adhesive 22, however, the body 30 and base sheet 20 may be attached to each other by any suitable technique or techniques, e.g., melt bonding, combinations of melt bonding and adhesives, etc. As used herein, a "melt bond" is a bond formed by the melting and/or mixing of materials such as that occurring during, e.g., heat sealing, thermal welding, ultrasonic welding, chemical welding, solvent bonding, etc. If melt bonded, it may be preferred that both the body 30 and the base sheet 20 include, e.g., polypropylene or some other melt bondable material at their interface to facilitate melt bonding.

It may, however, be preferred that the base sheet 20 be attached to the body 30 using adhesive. As depicted in FIG. 3, the adhesive may preferably be provided in the form of a layer 22. It may be preferred that the adhesive layer 22 be provided as a continuous, unbroken layer over the surface of at least one of the body 30 and the base sheet 20. It may, for example, be preferred that the adhesive layer 22 be provided on the base sheet and, more particularly, it may be preferred that the adhesive layer 22 cover substantially all of the surface of the base sheet 20 facing the body 30.

A variety of adhesives may be used, although any adhesive selected should be capable of withstanding the forces generated during processing of any sample materials located in the process chambers 50, e.g., forces developed during distribution of the sample materials, forces developed during thermal processing of the sample materials, etc. Those forces may be large where e.g., the processing involves thermal cycling as in, e.g., polymerase chain reaction and similar processes. It may also be preferred that any adhesives used in connection with the sample processing devices exhibit low fluorescence, be compatible be the processes and materials to be used in connection with sample processing devices, e.g. PCR, etc.

It may be preferred to use adhesives that exhibit pressure sensitive properties. Such adhesives may be more amenable to high volume production of sample processing devices since they typically do not involve the high temperature bonding processes used in melt bonding, nor do they present the handling problems inherent in use of liquid adhesives, solvent bonding, ultrasonic bonding, and the like.

One well known technique for identifying pressure sensitive adhesives is the Dahlquist criterion. This criterion defines a pressure sensitive adhesive as an adhesive having a 1 second creep compliance of greater than $1 \times 10^{-6}$ cm$^2$/dyne as described in *Handbook of Pressure Sensitive Adhesive Technology*, Donatas Satas (Ed.), 2$^{nd}$ Edition, p. 172, Van Nostrand Reinhold, New York, N.Y., 1989. Alternatively, since modulus is, to a first approximation, the inverse of creep compliance, pressure sensitive adhesives may be defined as adhesives having a Young's modulus of less than $1 \times 10^6$ dynes/cm². Another well known method of identifying a pressure sensitive adhesive is that it is aggressively and permanently tacky at room temperature and firmly adheres to a variety of dissimilar surfaces upon mere contact without the need of more than finger or hand pressure, and which may be removed from smooth surfaces without leaving a residue as described in *Test Methods for Pressure Sensitive Adhesive Tapes*, Pressure Sensitive Tape Council, (2000) pp. 23-30 and 32-34. Another suitable definition of a suitable pressure sensitive adhesive is that it preferably has a room temperature storage modulus within the area defined by the following points as plotted on a graph of modulus versus frequency at 25° C.: a range of moduli from approximately $2\times10^5$ to $4\times10^5$ dynes/cm² at a frequency of approximately 01 radian/second (0.017 Hz), and a range of moduli from approximately $2\times10^6$ to $8\times10^6$ dynes/cm2 at a frequency of approximately 100 radians/second (17 Hz) (for example see FIG. 8-16 on p. 173 of *Handbook of Pressure Sensitive Adhesive Technology*, Donatas Satas (Ed.), $2^{nd}$ Edition, Van Nostrand Rheinhold, New York, 1989). Any of these methods of identifying a pressure sensitive adhesive may be used to help identify potentially suitable pressure sensitive adhesives for use in the methods of the present invention.

It may be preferred that the pressure sensitive adhesives used in connection with the sample processing devices of the present invention include materials which ensure that the properties of the adhesive are not adversely affected by water. For example, the pressure sensitive adhesive will preferably not lose adhesion, lose cohesive strength, soften, swell, or opacify in response to exposure to water during sample loading and processing. Also, the pressure sensitive adhesive should not contain any components which may be extracted into water during sample processing, thus possibly compromising the device performance.

In view of these considerations, it may be preferred that the pressure sensitive adhesive be composed of hydrophobic materials. As such, it may be preferred that the pressure sensitive adhesive be composed of silicone materials. That is, the pressure sensitive adhesive may be selected from the class of silicone pressure sensitive adhesive materials, based on the combination of silicone polymers and tackifying resins, as described in, for example, "Silicone Pressure Sensitive Adhesives", *Handbook of Pressure Sensitive Adhesive Technology*, $2^{nd}$ Edition, pp. 508-517. Silicone pressure sensitive adhesives are known for their hydrophobicity, their ability to withstand high temperatures, and their ability to bond to a variety of dissimilar surfaces.

The composition of the pressure sensitive adhesives is preferably chosen to meet the stringent requirements of the present invention. Some suitable compositions may be described in International Publication WO 00/68336 titled SILICONE ADHESIVES, ARTICLES, AND METHODS (Ko et al.).

Other suitable compositions may be based on the family of silicone-polyurea based pressure sensitive adhesives. Such compositions are described in U.S. Pat. No. 5,461,134 (Leir et al.); U.S. Pat. No. 6,007,914 (Joseph et al.); International Publication No. WO 96/35458 (and its related U.S. patent application Ser. No. 08/427,788 (filed Apr. 25, 1995); Ser. No. 08/428,934 (filed Apr. 25, 1995); Ser. No. 08/588,157 (filed Jan. 17, 1996); and Ser. No. 08/588,159 (filed Jan. 17, 1996); International Publication No. WO 96/34028 (and its related U.S. patent application Ser. No. 08/428,299 (filed Apr. 25, 1995); Ser. No. 08/428,936 (filed Apr. 25, 1995); Ser. No. 08/569,909 (filed Dec. 8, 1995); and Ser. No. 08/569,877 (filed Dec. 8, 1995)); and International Publication No. WO 96/34029 (and its related U.S. patent application Ser. No. 08/428,735 (filed Apr. 25, 1995) and Ser. No. 08/591,205 (filed Jan. 17, 1996)).

Such pressure sensitive adhesives are based on the combination of silicone-polyurea polymers and tackifying agents. Tackifying agents can be chosen from within the categories of functional (reactive) and nonfunctional tackifiers as desired. The level of tackifying agent or agents can be varied as desired so as to impart the desired tackiness to the adhesive composition. For example, it may be preferred that the pressure sensitive adhesive composition be a tackified polydiorganosiloxane oligurea segmented copolymer including (a) soft polydiorganosiloxane units, hard polyisocyanate residue units, wherein the polyisocyanate residue is the polyisocyanate minus the -NCO groups, optionally, soft and/or hard organic polyamine units, wherein the residues of isocyanate units and amine units are connected by urea linkages; and (b) one or more tackifying agents (e.g., silicate resins, etc.).

Furthermore, the pressure sensitive layer of the sample processing devices of the present invention can be a single pressure sensitive adhesive or a combination or blend of two or more pressure sensitive adhesives. The pressure sensitive layers may result from solvent coating, screen printing, roller printing, melt extrusion coating, melt spraying, stripe coating, or laminating processes, for example. An adhesive layer can have a wide variety of thicknesses as long as it meets exhibits the above characteristics and properties. In order to achieve maximum bond fidelity and, if desired, to serve as a passivation layer, the adhesive layer should be continuous and free from pinholes or porosity.

Even though the sample processing devices may be manufactured with a pressure sensitive adhesive to connect the various components, e.g., sides, together, it may be preferable to increase adhesion between the components by laminating them together under elevated heat and/or pressure to ensure firm attachment of the components and sealing of the process arrays.

Figure 5:
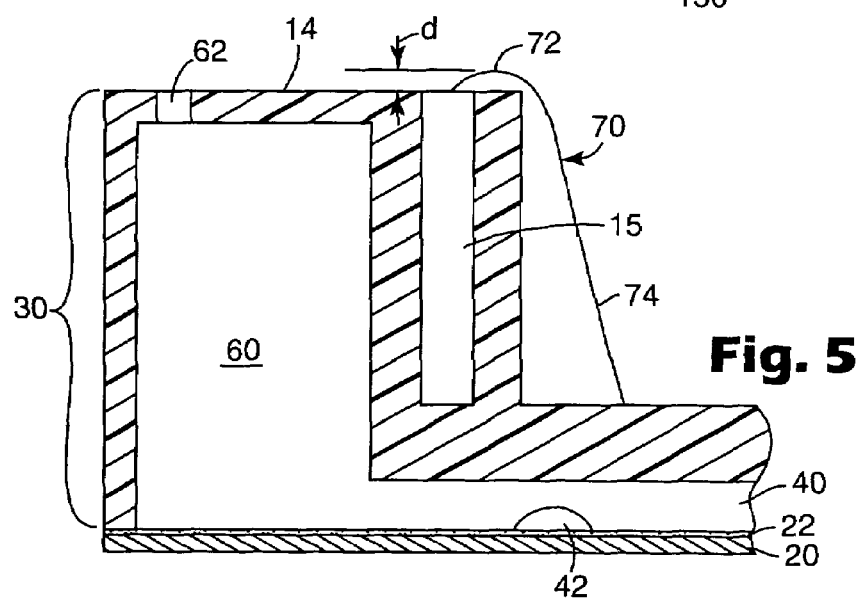
FIG. 5 is an enlarged cross-sectional view of a portion of the sample processing device of FIG. 1 including a fill reservoir and a portion of a channel used to distribute sample material from the fill reservoir to the process chambers.

FIG. 5 depicts a cross-sectional view of a portion of the sample processing device 10 including a fill reservoir 60 formed between the body 30 and the base sheet 20 (which is attached to the body 30 using adhesive 22). Also seen in FIG. 5 are a fill port 62 for loading the fill reservoir and a cavity 15 in the body 30 to reduce the thermal mass of the body 30.

A compression structure 70 is depicted and includes a peak 72 and a single rib 74 (which can be contrasted from the multi-ribbed compliances structures located within the array). As discussed with respect to FIG. 3, it may be preferred that the compression structures 70 extend above or protrude from a plane that is defined by the uppermost surface of the frame 14. The peaks 72 of the compression structures 70 are located a distance (d) above the frame 14 (or the plane defined by the frame 14). By extending above the frame 14 or any other structure on the sample processing device 10, the compression structures 70 are assured of contacting, e.g., a platen or other device used to urge the base sheet 20 against, e.g., a thermal block or on optical interrogation device.

FIG. 5 also depicts a main channel 40 in fluid communication with the fill reservoir 60. The main channel 40 is formed, in the depicted embodiment, primarily within the body 30, with the base sheet 20 located over the main channel structure to define the volume of the channel 40. Also seen in FIG. 5 is a feeder channel 42 extending off of the main channel 40.

Figure 6:
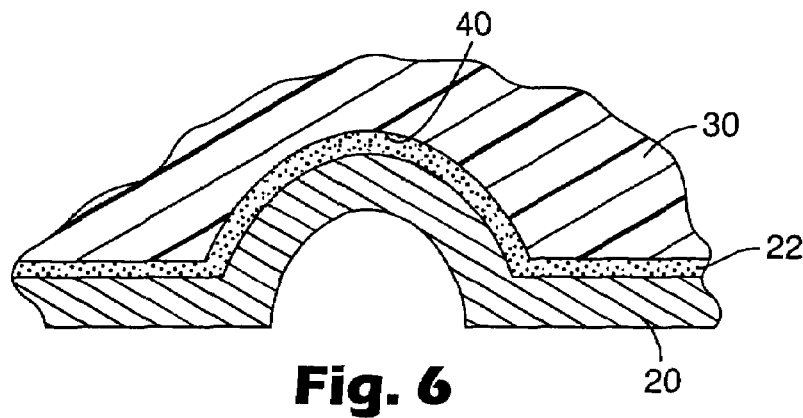
FIG. 6 is an enlarged cross-sectional view of an occluded channel in accordance with the principles of the present invention.

Referring to FIG. 6, a cross-sectional view of a main channel 40 is depicted to illustrate another potential feature of the sample processing devices of the invention, namely a deformable seal that may be used to close the main channel 40, isolate the process chambers 50, or accomplish both closure of the main channel 40 and isolation of the process chambers 50.

The main channel 40 is sealed or occluded by forcing the base sheet 20 into the channel 40. In some instances, the material of the base sheet 20 will undergo plastic deformation. In other instances, the adhesive 22 alone may be enough to retain the base sheet 20 in contact with the surface of the channel 40 sufficiently to occlude the channel 40 (with the base sheet 20 undergoing only elastic deformation). Any conformability in the adhesive 22 may allow it to conform and/or deform to more completely fill and occlude the channel being occluded. It may be preferred that the adhesive 22 be a pressure sensitive adhesive, although a hot melt adhesive may alternatively be used if deformation of the base sheet 20 is accompanied by the application of thermal energy sufficient to activate the hot melt adhesive.

It should be understood that complete sealing or occlusion of the deformed portions of the sample processing device 10 may not be required. For example, it may only be required that the deformation restrict flow, migration or diffusion through a conduit or other fluid pathway sufficiently to provide the desired isolation. As used in connection with the present invention, "occlusion" will include both partial occlusion and complete occlusion (unless otherwise explicitly specified).

As used in connection with the present invention, the deformable seals may be provided in a variety of locations and/or structures incorporated into the sample processing devices. Essentially, however, the deformable seal in a process array will be located somewhere in the fluid path between the loading chamber and the plurality of process chambers. Occlusion of the main channel may be continuously over substantially all of the length of the main channel or it may be accomplished over discrete portions or locations along the length of the main channel. Also, closure of the deformable seal may be accomplished by occlusion of the feeder channels alone and/or by occlusion of the feeder channel/main channel junctions (in place of, or in addition to, occlusion of a portion or all of the length of the main channel).

With respect to FIG. 1, for example, the deformable seal may be located in the main channel 40 between the fill reservoir 60 and the process chambers 50 of each process array. In this configuration the deformable seal may extend for the substantially the entire length of the main channel 40 or it may be limited to selected areas. For example, the deformable seal may extend along the main channel 40 only in the areas occupied by the feeder channels 42 leading to the process chambers 50. In another example, the deformable seal may be a composite structure of discrete sealing points located along the main channel 40 or within each of the feeder channels 42. In another configuration, the deformable seal may be limited to the area between the fill reservoirs 60 and the process chambers 50 in each of the process arrays.

In some embodiments it may be advantageous to occlude the main channel over substantially all of its length and, in so doing, urge any sample materials within the main channel back towards the fill reservoir 60. It may be preferred that the sample materials urged back towards the fill reservoir are driven back into the fill reservoir. As a result, the fill reservoirs in process arrays of the present invention may also serve as waste or purge chambers for sample materials urged out of the main channels and/or feeder channels during closure of the deformable seals.

Figure 7:
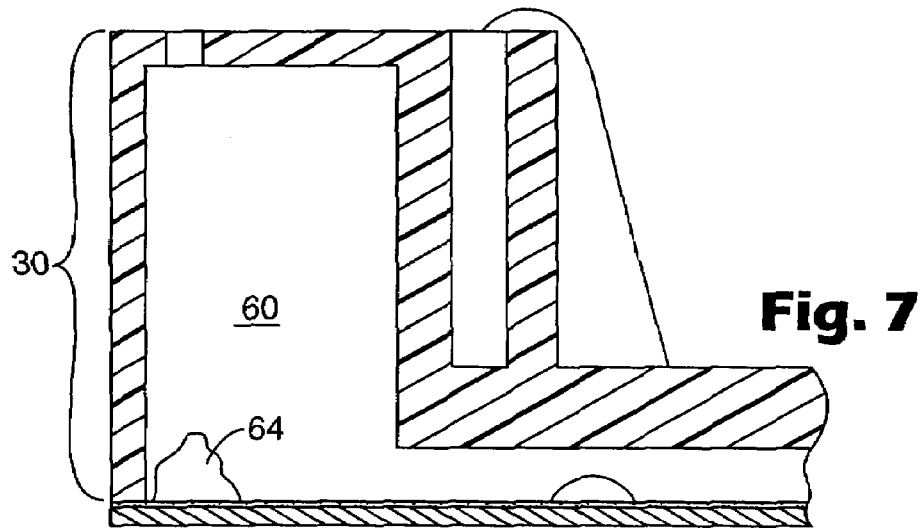
FIG. 7 is the view of FIG. 5 in which a portion of a wall separating the fill reservoir from an adjacent fill reservoir has been removed to place the fill reservoirs in fluid communication with each other.
Figure 8:
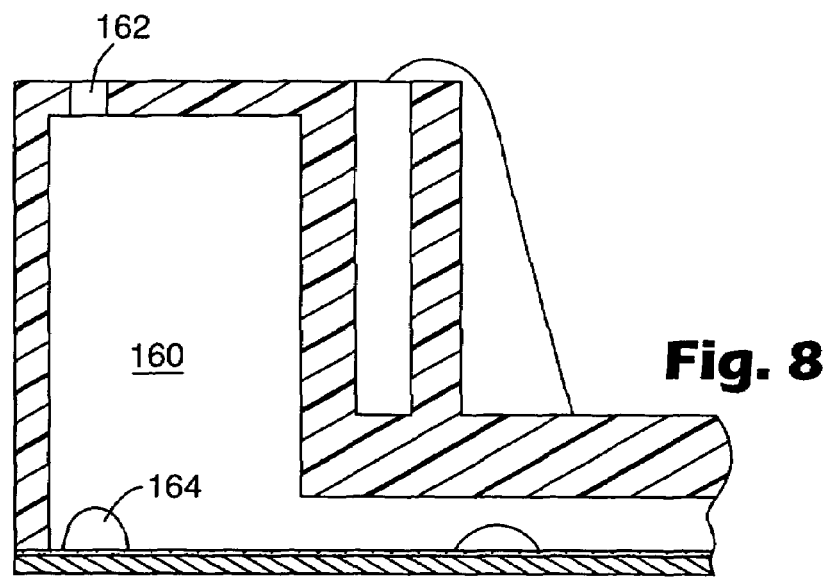
FIG. 8 is a cross-sectional view of an alternative sample processing device including a fill reservoir with a fluid pathway to an adjacent fill reservoir.

FIGS. 7 & 8 depict variations in the fill reservoir structures. Referring first to FIG. 7, the fill reservoir 60 of FIG. 5 is depicted with an fluid path 64 provided in the common wall that the reservoir shares with its adjacent fill reservoir (see, e.g., FIG. 2). The fluid path 64 can be formed by removing a portion of the wall such that the two fill reservoirs are no longer isolated from each other, thereby providing a common fill reservoir for two process arrays on the sample processing device 10. Removal of the wall portion may be accomplished by, e.g., using a forceps, pliers or other device or technique. This method will typically be accomplished by removing the portion before the base sheet 20 is attached to the body 30.

The fill reservoir 160 of FIG. 8 includes a fluid path 164 formed in the wall between what would otherwise be two isolated fill reservoirs. In this embodiment, the opening may be occluded by a deformable seal as described above with the respect to the channels. In other words, the fill reservoir structures may be isolated from each other by forcing the base sheet 120 into the fluid path 164 such that the fluid path 164 is occluded. In this manner, a sample processing device in which fill reservoir structures are in fluid communication with each other may be customized by selectively occluding the fluid paths between the fill reservoir structures. For example, all of the fill reservoirs 60 located along edge 11 of the sample processing device 10 in FIG. 1 may be in fluid communication through fluid paths similar to fluid path 164. The fill reservoirs 60 may then be selectively isolated to provide a customized sample processing device according to the present invention.

Figure 9:
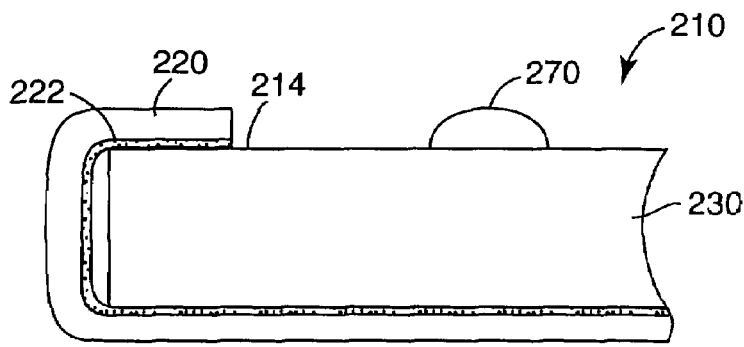
FIG. 9 is a side elevational view of an alternative sample processing device depicting one technique of sealing fill reservoirs.

FIG. 9 is a side elevational view of a portion of another sample processing device according to the present invention. The sample processing device 210 includes a body 230 and a base sheet 220 that, in the depicted embodiment, is attached to the body 230 by a layer of adhesive 222. The body includes a frame 214 and compression structures 270 extending above the frame 214.

One difference between the sample processing device 210 and the sample processing device 10 described above is that the base sheet 220 extends past the boundaries or footprint of the body 230. As a result, the base sheet 220 can be wrapped around the frame 214 of the body 230 to, e.g., seal any fill ports (not shown in FIG. 9) that lead into fill reservoirs (also not shown in FIG. 9). This sealing technique may be used in place of, e.g., a separate adhesive tape as discussed above.

Although the base sheet 220 is depicted as including a continuous layer of adhesive 222, it will be understood that the base sheet 220 may be attached to the bottom of body 230 by any suitable technique (adhesive or otherwise). It will also be understood that the adhesive used to attach the base sheet extension (i.e., that portion of the base sheet 220 that extends beyond the body 230) to the upper side of the body 230 may be the same adhesive (as shown) or a different adhesive. Although not shown, a release liner may be provided to protect the adhesive 222 before it is used to seal the fill ports.

Figure 10:
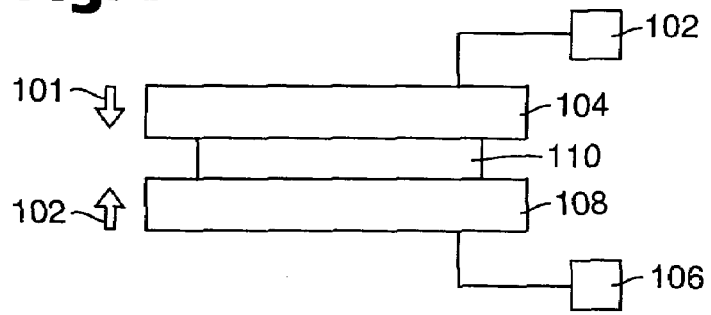
FIG. 10 is a block diagram of one thermal processing system that may be used in connection with the sample processing devices of the present invention.

FIG. 10 depicts one thermal processing system that may be used in connection with the sample processing devices of the present invention in a block diagram format. The system includes an sample processing device 110 located on a platform 108, which may be, e.g., a thermal block. If platform 108 is a thermal block, the temperature of the platform 108 is preferably controlled by a thermal controller 106. On the opposite side of the sample processing device 110, a platen 104 is provided to urge the sample processing device 110 into intimate contact with the platform 108. The temperature of the platen 104 may be thermally controlled (if desired) by a thermal controller 102 (that may, in some instances, be the same as a controller 106 controlling the temperature of the thermal block 108). The sample processing device 110 is compressed between the platen 104 and platform 108 as indicated by arrows 101 and 102 during thermal processing of the sample processing device 110.

In alternative systems, the block 108 may, instead, be an optical interrogation platform 108 against which the sample processing device 110 is urged to improve optical coupling of the process chambers in the sample processing device 110 with the optical components in the interrogation platform 108. In such a system, the sample processing device 110 would preferably include a base sheet that transmits the electromagnetic energy used for interrogation. The interrogation platform 108 may be in optical or other communication with an interrogation system controller 106. Such an interrogation system may be used for "end-point reads" if the sample processing device 110 is processed using, e.g., thermal sinks such as fluid baths or other systems that do not include a thermal block and/or do not provide for integrated interrogation of the sample processing device 110.

Figure 11A:
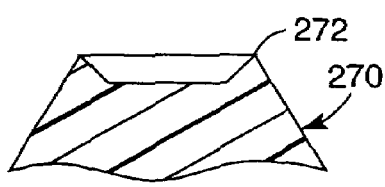
FIGS. 11A & 11B depict one example of a frangible element for a compression structure of the present invention.
Figure 11B:
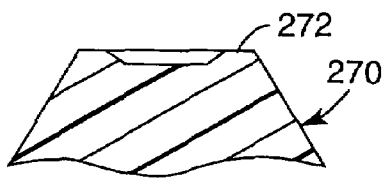

As discussed above, the compression structures of the sample processing devices of the present invention may provide a variety of different functions. FIGS. 11A & 11B depict an isolated view of one embodiment of a compression structure 270 that includes a ridge 272. FIG. 11B illustrates the ridge 272 after permanent deformation.

The ridge 272 is one form of a frangible element located on a compression structure in accordance with the present invention. The ridge 272 may preferably be constructed to permanently deform upon the application of sufficient pressure by, e.g., a platen. That deformation can provide a number of functions. For example, it can provide an indication that the sample processing device on which the compression structure 270 is located has been used. The deformation can also provide some level of equilibration in the applied forces. For example, manufacturing tolerances may result in different heights between different compression structures. Those variations may, however, be moderated by varying deformation of the ridges 272 on different compression structures 270.

In other words, taller compression structures may experience more deformation, while shorter compression structures may experience less deformation. It may be preferred that the dimensions of the compression structures be selected such that all of the compression structures will experience at least some deformation to ensure that all of the compression structures are used to transmit force to the base sheet of the sample processing devices. In other words, the compression structures may improve compliance of the sample processing device, thereby enabling better thermal contact to the heating platen.

Figure 12A:
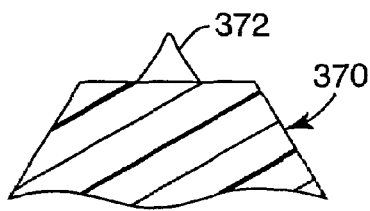
FIGS. 12A & 12B depict another example of a frangible element for a compression structure of the present invention.
Figure 12B:
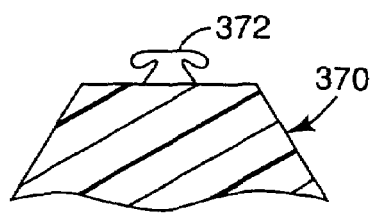

FIGS. 12A & 12B depict another example of a frangible element 372 on a compression structure, with FIG. 12A depicting the frangible element 372 before deformation and FIG. 12B depicting the frangible element 372 after deformation.

Figure 13:
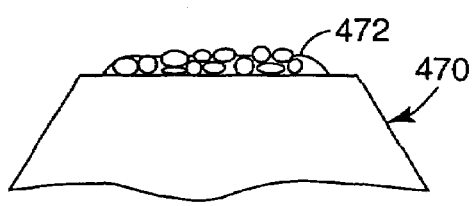
FIG. 13 depicts another example of a frangible chromic indicator for a compression structure of the present invention.

FIG. 13 depicts another frangible element 472 on a compression structure 470. The frangible element 472 may include a chromic indicator, e.g., beads, etc. that rupture under pressure or are otherwise modified such that a color change occurs after the application of pressure on the compression structure 470.

Figure 14:
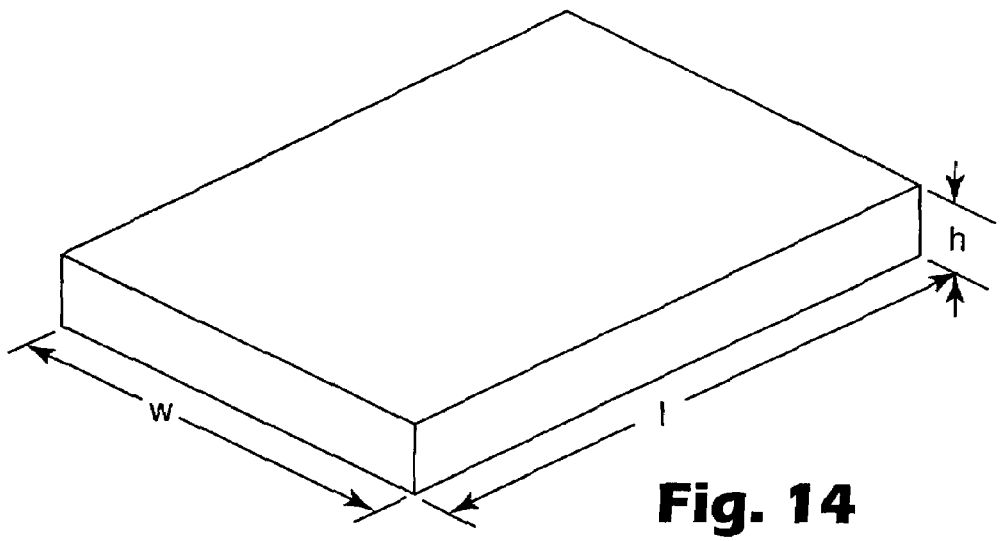
FIG. 14 is a perspective view of a preferred form factor for a sample processing device according to the present invention.

FIG. 14 depicts the form factor that a sample processing device according to the present invention may preferably take. It may be preferred that the height (h) of the sample processing devices of the invention comply with the height requirements as discussed by the Society for Biomolecular Screening Standard "SBS-2 for Microplates—Height Dimensions" (9 May 2002). That standard sets forth a maximum height of 14.35 millimeters (±0.25 millimeters). At the lower end of the range, it may be preferred that the height of sample processing devices according to the present invention be 5 millimeters or more. A minimum height may be beneficial to assist in handling of the sample processing devices by, e.g., robotic handling systems.

It may also be preferred that the footprint dimensions, that is the length (l) and the width (w) comply with the footprint requirements as discussed by the Society for Biomolecular Screening Standard "SBS-1 for Microplates—Footprint Dimensions" (17 Jan. 2002). That standard sets forth a length of 127.76 millimeters (±0.25 millimeters) and a width of 85.48 millimeters (±0.25 millimeters). Unlike the height dimension, it may not be desirable to provide sample processing devices with a significantly different footprint because most, if not all, conventional microplate processing systems are designed to process devices with the footprint identified above. Although conventional systems may readily use sample processing devices that do not reach the maximum height specified in the standard, they may not be readily adaptable for use with devices having a different footprint.

Figure 15:
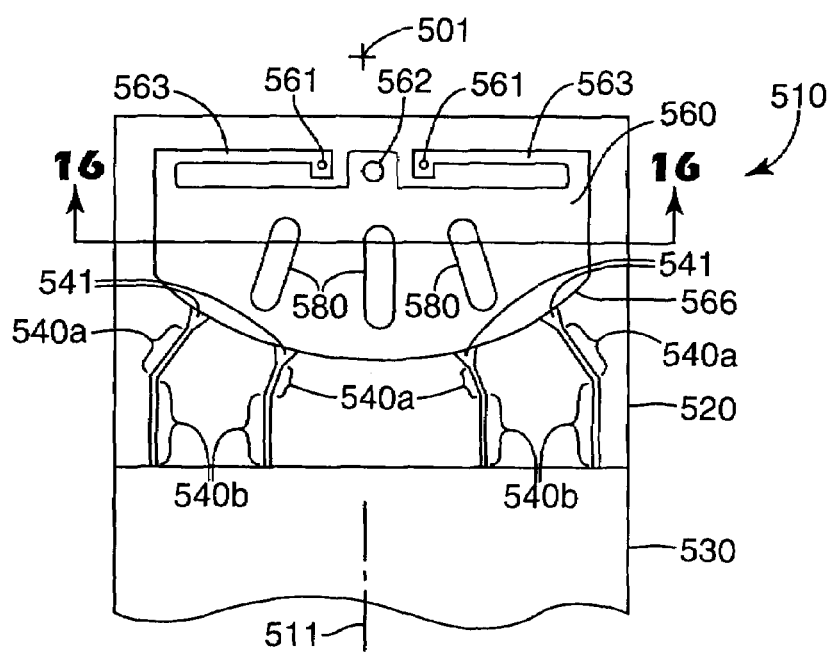
FIG. 15 is a plan view of another alternative sample processing device according to the present invention.
Figure 16:
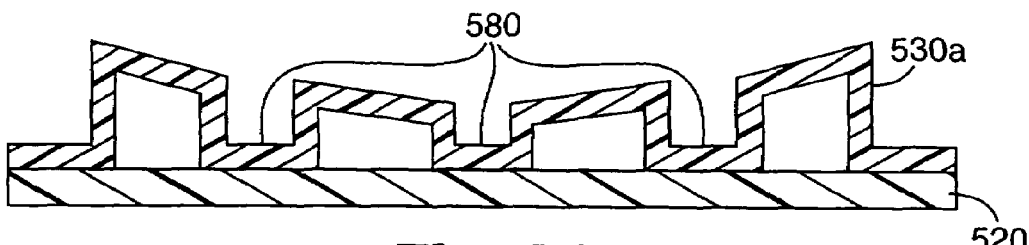
FIG. 16 is a cross-sectional view of the fill reservoir of the sample processing device of FIG. 15, taken along line 16-16 in FIG. 15.

FIG. 15 is a plan view of a portion of another alternative sample processing device 510 according to the present invention and FIG. 16 is a cross-sectional view taken along line 16-16 in FIG. 15. Only a portion of the sample processing device 510 is seen in the figures, with the base sheet 520 extending past the footprint of the body 530 along one edge of the body 530 (see, e.g., FIG. 9 above for a side elevational view of a similar base sheet extension). A cover 530a is attached to the base sheet 520 where it extends past the body 530.

In this embodiment, the base sheet 520 and cover 530a may be, e.g., a laminated construction similar to those described in, e.g., U.S. patent application Ser. No. 09/895,001, filed 28 Jun. 2001, and titled SAMPLE PROCESSING DEVICES AND CARRIERS (corresponding to International Publication No. WO 02/01181 A2 (Bedingham et al.); and U.S. patent application Ser. No. 09/895,010, filed 28 Jun. 2001, and titled SAMPLE PROCESSING DEVICES (corresponding to International Publication No. WO 02/01180 A2 (Bedingham et al.). As a result, one or both of the laminated layers can be formed to provide a volume therebetween. In the depicted embodiment, that cover 530a is formed to provide a fill reservoir 560, funnels 541, and channels 540a and 540b that lead to the main channels (not shown) formed within the bounds of the body 530 as discussed above. Alternatively, the features may be formed in the base sheet 520 or in both the cover 530a and the base sheet 520.

The single fill reservoir 560 is used to load multiple main channels in the sample processing device 510. It may be preferred that the sample processing device 510 include only one fill reservoir 560, although more than one fill reservoir feeding two or more channels may be used in connection with the present invention.

The fill reservoir 560 and associated channels are designed in a manner that may provide several advantages if the sample materials are to be loaded into the process chambers of the sample processing device using centrifugal forces. For example, the arcuate edge 566 of the fill reservoir 560 may preferably be designed to follow a circular arc having a radius defined by the location of the axis of rotation 501 about which sample processing device 510 is rotated to deliver sample materials from the fill reservoir 560 to the channels. Minor variations from a true circular arc may be tolerated within the scope of the invention unless otherwise specified. That arcuate edge design may, for example, result in a radial vector alignment of the liquid flow front as it enters the funnels 541 feeding the channels 540a to provide essentially uniform flow into all channels due to the balanced hydrostatic equilibrium along the curved edge 566 of the fill reservoir 560. In contrast, a fill reservoir with a flat front edge (i.e., the edge facing away from the axis of rotation 501) may experience fluid starvation to one or more channels during loading by centrifugation.

Another feature of the design depicted in FIG. 15 is the orientation of the funnels 541 and channels 540a that are in direct fluid communication with the fill reservoir 560. As discussed above, the edge 566 of the fill reservoir 560 may preferably have a curvature defined by the axis of rotation 501. To further promote even flow of sample material out of the fill reservoir 560, each of the channels 540a (and associated option funnels 541) exits the fill reservoir 560 from the arcuate edge 566 and may preferably be aligned radially with respect to the axis of rotation 501. As a result, the channels 540a are normal to a tangent of the arcuate edge 566 of the fill reservoir 560. One potential advantage of this arrangement is that the fluid force vectors developed during centrifugation about the axis 501 are aligned with the channels 540a, further enhancing even flow out of the fill reservoir 560.

The radially-aligned channels 540a may, however, preferably transition to channels 540b that are generally aligned with a longitudinal axis 511 to match the arrangement of main channels (not shown) within the body 530 of the sample processing device 510. Those main channels are, as described above, preferably parallel with each other to facilitate staking or closure of the main channels to reduce fluid movement between process chambers during processing.

The larger fill reservoir 560 may include support structures 580 within its boundaries to prevent collapse during handling and processing. The support structures 580 may be elongated as shown (i.e., have a length greater than their width) or take any other desired shape. The elongated support structures 580 may be aligned with the longitudinal axis 511 of the sample processing device 510 or they may alternatively be aligned radially as are channels 540a (i.e., normal to a tangent of the arcuate edge 566). As depicted in FIG. 16 (a cross-sectional view of FIG. 15 taken along line 16-16), the support structures 580 may be formed in the cover 530a forming the fill reservoir 560 if it is of the laminated construction discussed above. In any design, however, the support structures are provided as intermediate support within the boundaries of the fill reservoir 560 to, e.g., reduce the likelihood of collapse of the fill reservoir 560 due to handling or suction forces that may develop during distribution of the sample material from the fill reservoir to the process chambers in the device 510.

Another feature depicted in FIG. 15 is fill port 562 that may be used to load sample material into the fill reservoir 560. Also seen in FIG. 15 are vent ports 561 connected to the main portion of the fill reservoir 560 by vent channels 563. The fill reservoir 560 preferably has a shape and construction that is symmetrical about the longitudinal axis 511 of the sample processing device 510. The symmetrical fill reservoir 560 also preferably includes a fill port 562 that is located along the longitudinal axis 511 of the sample processing device 510.

Multiple vent ports 561 are preferably provided in the fill reservoir 560 in a symmetrical arrangement with respect to the fill port 562 and the overall shape of the fill reservoir 560. It may be preferred that the vent ports 561 be located proximate the longitudinal axis 511 of the sample processing device 510 to along vent channels 563 that open into the main body of the fill reservoir 560 at points arranged symmetrically with respect to the longitudinal axis 511 (which is also the axis of symmetry for the fill reservoir 560). Another feature of the vent ports 561 is that they are preferably located on the opposite side of the fill port 562 with respect to the channels 540a to, e.g., reduce the likelihood of leakage from the vent ports 561 during centrifugal loading.

Isolating the vent ports 563 from the main portion of the fill reservoir 560 may reduce or eliminate leakage of sample material from the vent ports 561 during handling of the sample processing device 510. Also, the symmetric nature of the vent ports 561 and vent channels 563 may enhance even loading of sample material into the fill reservoir 560 and even fluid flow out of the fill reservoir 560 during centrifugation of the sample processing device 510.

As an alternative to, or in addition to the arcuate edge design for the fill reservoir 560, the height of the reservoir between the two sides of the fill reservoir may also be selectively varied such that a desired distribution of the volume of the fill reservoir is provided. That volumetric distribution can then be used to achieve a corresponding distribution of fluid sample material within the fill reservoir to, e.g., cause the sample material to pool preferentially towards the outer edges of the device.

This feature is illustrated in the cross-sectional view of FIG. 16, wherein the height of the fill reservoir 560 is greater proximate the outer edges of the fill reservoir 560 (i.e., distal from the center of the fill reservoir 560) than the height of the reservoir 560 proximate its center. That feature may be particularly useful if the fill reservoir is symmetric about an axis (such as axis 511 as seen in FIG. 15). The increased volume of the fill reservoir 560 proximate its outer edges may reduce or prevent fluid starvation that could hinder even filling of all of the distribution channels in a sample processing device of the present invention.

This same concept, i.e., fill reservoirs with differential volumes may be used in connection with any sample processing device according to the present invention. For example, if the fill reservoirs 60 in the sample processing device 10 of FIGS. 1 & 2 are in fluid communication with each other (as described above, e.g., in connection with FIGS. 7 & 8) the fill reservoirs 60 may preferably be provided with different volumes to reduce fluid starvation in the outermost reservoirs 60. For example, the outermost fill reservoirs 60 (those closest to sides 12 and 15) may be larger in volume than the fill reservoirs 60 closer to the center of the fill reservoir structure. Further, the fill reservoirs 60 may be designed such that any fluid within the fill reservoirs 60 is preferentially distributed towards the outermost fill reservoirs 60 when the sample processing device 10.

Patents, patent applications, and publications disclosed herein are hereby incorporated by reference as if individually incorporated. It is to be understood that the above description is intended to be illustrative, and not restrictive. Various modifications and alterations of this invention will become apparent to those skilled in the art from the foregoing description without departing from the scope of this invention, and it should be understood that this invention is not to be unduly limited to the illustrative embodiments set forth herein.

The invention claimed is:

1. A sample processing device comprising:
   a fill reservoir,
   a plurality of process chambers; and
   a plurality of channels, wherein each channel of the plurality of channels is in fluid communication with the fill reservoir and wherein each process chamber of the plurality of process chambers is in fluid communication with at least one channel of the plurality of channels;
   wherein the fill reservoir comprises an arcuate edge, wherein each channel of the plurality of channels exits the fill reservoir from the arcuate edge of the fill reservoir, wherein each channel of the plurality of channels extends in a direction normal to a tangent of the arcuate edge for a first portion of the length of the channel, and wherein the plurality of channels are aligned with a longitudinal axis for a second portion of the length of the channel.

2. A device according to claim 1, wherein the fill reservoir comprises an axis of symmetry, and wherein the fill reservoir comprises:
   a fill port proximate the axis of symmetry; and
   two or more vent ports arranged symmetrically about the axis of symmetry.

3. A device according to claim 2, wherein the vent ports are in fluid communication with the fill reservoir through vent channels, with the vent channels connected to the fill reservoir at points symmetrical with the axis of symmetry.

4. A device according to claim 1, wherein the fill reservoir comprises a fill port and one or more vent ports, and further wherein the one or more vent ports are located on a side of the fill reservoir that is opposite from the side on which the channels are located.

5. A device according to claim 1, further comprising one or more support structures located within the fill reservoir, wherein the support structures maintain spacing between two opposing sides of the fill reservoir.

6. A device according to claim 5, wherein the support structures are elongated and arranged along a direction normal to a tangent of the arcuate edge.

7. A device according to claim 1, wherein the fill reservoir comprises a selectively varied height between two sides of the fill reservoir such that a desired distribution of the volume of the fill reservoir is provided.

8. A device according to claim 7, wherein the fill reservoir comprises a center and outer edges distal from the center, and wherein the height of the fill reservoir proximate the outer edges is greater than the height of the fill reservoir proximate the center.

9. A device according to claim 1, wherein each channel of the plurality of channels is in fluid communication with the arcuate edge of the fill reservoir through a funnel.

10. A method of processing sample materials, the method comprising:
   providing a sample processing device according to claim 1;
   loading the fill reservoir with sample material;
   rotating the sample processing device about an axis of rotation located proximate a center defined by the arcuate edge of the fill reservoir and the first portions of the channels, whereby the sample material is distributed to the plurality of process chambers.

* * * * *

UNITED STATES PATENT AND TRADEMARK OFFICE
CERTIFICATE OF CORRECTION

PATENT NO. : 7,507,376 B2 Page 1 of 1
APPLICATION NO. : 10/325723
DATED : March 24, 2009
INVENTOR(S) : Joel R. Dufresne It is certified that error appears in the above-identified patent and that said Letters Patent is hereby corrected as shown below:

<u>Column 15</u>
Line 14, Delete "01" and insert -- 0.1 --, therefor.
Line 16, Delete "dynes/cm2" and insert -- dynes/cm$^2$ --, therefor.

<u>Column 22</u>
Line 55, In Claim 1, delete "reservoir," and insert -- reservoir; --, therefor.

Signed and Sealed this

Thirtieth Day of June, 2009

JOHN DOLL
*Acting Director of the United States Patent and Trademark Office*